United States Patent
Chang

(10) Patent No.: US 7,329,625 B2
(45) Date of Patent: Feb. 12, 2008

(54) ATTRITION RESISTANT MOLECULAR SIEVE CATALYST

(75) Inventor: Yun-feng Chang, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/588,552

(22) Filed: Oct. 27, 2006

(65) Prior Publication Data

US 2007/0100187 A1    May 3, 2007

Related U.S. Application Data

(60) Provisional application No. 60/732,546, filed on Nov. 2, 2005.

(51) Int. Cl.
*B01J 27/182* (2006.01)
*B01J 27/18* (2006.01)
*B01J 29/06* (2006.01)
*C07C 1/20* (2006.01)

(52) U.S. Cl. ............... 502/60; 502/208; 502/214; 585/638; 585/639; 585/640

(58) Field of Classification Search ............ 502/60, 502/208, 214; 585/638, 639, 640
See application file for complete search history.

(56) References Cited

U.S. PATENT DOCUMENTS 6,153,552 A    11/2000  Wachter et al.
6,787,501 B2 *  9/2004  Vaughn et al. ............ 502/214

FOREIGN PATENT DOCUMENTS

| WO | WO 99/21651    | 5/1999  |
|----|----------------|---------|
| WO | WO 03/000413   | 1/2003  |
| WO | WO 03/068395   | 8/2003  |
| WO | WO 2004/060559 | 7/2004  |
| WO | WO 2004/105942 | 12/2004 |
| WO | WO 2005/039761 | 5/2005  |

* cited by examiner

*Primary Examiner*—Elizabeth D. Wood

(57) ABSTRACT

This invention provides a process for making an attrition resistant molecular sieve catalyst composition. The formation of highly attrition resistant catalyst particles is accomplished by initially mixing together catalyst components to form a slurry at a relatively low viscosity and high solids content. Preferably, a slurry having characteristics of high solids content and low viscosity is achieved using a rotor-stator mixer. Once the desired slurry characteristics are obtained, the slurry is dried, preferably by spray drying and calcining, to form a highly attrition resistant catalyst.

30 Claims, No Drawings

ATTRITION RESISTANT MOLECULAR SIEVE CATALYST

CROSS REFERENCE TO RELATED APPLICATION

This application claims priority to Provisional application filed on Nov. 2, 2005, U.S. Ser. No. 60/732,546.

FIELD OF THE INVENTION

This invention relates to methods of making and using molecular sieve catalyst. In particular, the invention relates to methods of making and using metalloaluminophosphate molecular sieve catalyst that is highly attrition resistant.

BACKGROUND OF THE INVENTION

A desirable characteristic for certain molecular sieve catalysts, regardless of the process of use, is that the finished or formulated catalyst be attrition resistant. Attrition resistance can refer to hardness as well as ability to absorb shock, since the catalyst will typically have to endure severe stress in commercial scale processes.

For example, WO 99/21651 describes a method for making molecular sieve catalyst that is considered relatively hard. The method includes the steps of mixing together a molecular sieve and an alumina sol, the alumina sol being made in solution and maintained at a pH of 2 to 10. The mixture is then spray dried and calcined. The calcined product is reported to be relatively hard.

U.S. Pat. No. 6,153,552 describes another method for making molecular sieve catalyst. The catalyst is made by mixing together a silicon containing oxide sol as a binder material and a molecular sieve material. The pH of the mixture is adjusted prior to spray drying. Following spray drying, the catalyst material is calcined to form a finished catalyst product, which is reported to be relatively hard.

Attrition resistance continues to be a desirable characteristic in molecular sieve catalysts. As new process systems are developed, the ability of the catalyst to endure the stress of the process system is particularly important so as to increase the effective life of the catalyst in the reaction process. If the catalyst is not properly attrition resistant, it is likely to break apart at an early stage, meaning that the catalyst could only be effectively used for a relatively short period of time. Therefore, obtaining molecular sieve catalysts that have a high degree of attrition resistance are still sought. Methods that are particularly effective at making highly attrition resistant molecular sieve catalysts at commercial scale are in particularly high demand.

SUMMARY OF THE INVENTION

This invention provides methods for making and using highly attrition resistant molecular sieve catalyst. The methods are particularly effective at commercial scale manufacture. In general, the methods include making a slurry of catalyst components at relatively high solids content and low viscosity using a rotor-stator mixer, then drying the slurry to form the finished catalyst.

According to one aspect of the invention, there is provided a method of making an attrition resistant molecular sieve catalyst composition. The method comprises mixing together molecular sieve crystals, clay, binder and liquid with a rotor-stator mixer to form a slurry having a solids content of at least 40 wt %, based on total weight of the slurry.

In one embodiment, the rotor and stator have a gap distance of not greater than 0.3 mm. Preferably, the stator has at least one hole defining an opening of not greater than 9 $mm^2$.

In another embodiment, slurry mixing is progressed until the slurry viscosity decreases to a noticeable extent. Preferably, the mixing is progressed until the viscosity is decreased by at least about 10%, more preferably by at least 15%, and most preferably by at least 10%.

In one embodiment, the molecular sieve crystals, clay, binder and liquid are mixed to form a slurry having a viscosity of not greater than 10,000 cP. After thorough mixing, the slurry product is preferably dried to produce a dried molecular sieve catalyst composition having an attrition rate index of not greater than 2 wt %/hr.

The dried catalyst composition can be used in any variety of processes. One preferred process is for use in the manufacture of olefins, wherein the dried molecular sieve catalyst is contacted with oxygenate to form olefin product.

In one embodiment, the stator includes at least one polygonal shaped hole. Prefearbly, the at least one polygonal shaped hole has at least one angle not greater than 90 degrees. More preferably, the at least one polygonal shaped hole is a rectangle. In a particular embodiment, the at least one polygonal shaped hole is a square.

The rotor is rotated at a speed sufficient to provide thorough mixing, preferably at a speed where viscosity of the slurry decreases as the slurry components are mixed. In one embodiment, the rotor is rotated at a tip speed of at least 5 m/sec.

The slurry can be dried by a combination of spray drying and calcining. Preferably, the slurry is dried using a spray dryer and the spray dried product is calcined.

In one embodiment, the molecular sieve particles are metalloaluminophosphate molecular sieve crystals.

DETAILED DESCRIPTION OF THE INVENTION

I. Forming a High Solids, Low Viscosity Slurry

This invention provides a process for making an attrition resistant molecular sieve catalyst composition. The process includes mixing together the catalyst components with liquid to form a slurry, and drying the slurry to form the catalyst.

The formation of highly attrition resistant catalyst particles is accomplished by initially making a slurry having a relatively high solids content. In particular, the slurry is mixed to a relatively low viscosity, taking into consideration the high solids content. Then the slurry is dried, preferably by spray drying and calcining, to form a highly attrition resistant catalyst.

According to this invention, attrition resistant refers to the ability to resist breaking apart as a result of physical impact. Since molecular sieve catalysts are often used in fluidized-bed reaction systems or riser-type reaction systems, the ability of such catalysts to avoid physical damage within the reaction systems is important. Attrition resistance, however, does not necessarily mean that the catalyst is hard, although hardness is a desirable characteristic. Attrition resistance can also be obtained through such characteristics as a catalyst's ability to absorb shock from impact as the catalyst is circulated through the reaction system. In some sense, the ability of the catalyst to absorb shock is similar to the ability of a ball to bounce off a hard surface with deforming the ball.

The catalyst formed by the process of this invention is particularly attrition resistant.

II. Method of Mixing Slurry Components

This invention includes a method or step of mixing together catalyst components and liquid to form a slurry having a high solids content and a relatively low viscosity. This mixing method or step is successfully accomplished using a desired mixer having certain appropriate settings.

As is understood by those of skill in the art, selecting an efficient mixer for a particular task can be a major component to successful processing, and processing technique has come to play an increasingly vital role in maintaining competitive advantage and profit margins. Therefore, choosing the right mixer for a particular mixing process can be a somewhat complex task, and huge variations in applications have led to a particularly diverse array of mixing equipment.

In the manufacture of molecular sieve catalysts, slurries are made of molecular sieve crystals and liquid (e.g., water), and possibly numerous other ingredients depending upon the characteristics desired of the finished catalyst product. These slurries are then dried to form a final or formulated molecular sieve product. The slurry that is ultimately dried to form the final molecular sieve product can vary widely in characteristics.

According to this invention, a slurry having characteristics of high solids content and low viscosity is achieved using a rotor-stator mixer. Rotor-stator mixers generally include a high-speed centrifugal-type rotor mounted within a stator. Typically, the stator is held in place by frame arms.

During operation, high-speed rotor revolution creates a suction that draws a mixture of liquid and solid materials into the center of the workhead assembly, where the mixture is subjected to a shear force, or it is assisted by external means (e.g., by using a feed pump). Centrifugal force then drives the materials to the periphery of the workhead, where the mixture encounters milling action in the clearance between the rotor blade tips and the stator inner wall. Hydraulic shear follows as the materials are forced out through the openings in the stator and are projected radially back into the body of the mixture.

The size and shape of openings in the stator (often referred to as the stator geometry) and the clearance between the rotor blade tips and the stator inner wall (typically referred to as gap distance) determine the flow pattern and the machine's shear rates. For example, a stator with round holes gives a type of mixing action that is particularly suited for disintegrating solids and preparing gels, suspensions, and solutions. Slotted holes produce a somewhat scissor-like shearing action that is particularly appropriate for disintegrating elastic or fibrous materials. Fine screens are typically used where a high degree of particle- or globule-size reduction is desired and for preparation of fine colloidal suspensions and emulsions.

In this invention the rotor and stator are arranged so that very high solids slurry compositions can be prepared at relatively low viscosities. An advantage in making high solids, low viscosity slurries is that in the preparation of molecular sieve catalyst compositions, a dried product of this type of slurry can be highly attrition resistant. In one embodiment of this invention, the rotor and stator have a gap distance of not greater than 0.3 mm, preferably 0.28 mm. In another embodiment, the rotor and stator have a gap distance of not greater than 0.25 mm, more preferably not greater than 0.2 mm, and most preferably not greater than 0.15 mm.

In another embodiment of the invention, the stator has at least 4 holes per square inch of surface area. Preferably, the stator has at least 6 holes per square inch of surface area, more preferably at least 8 holes per square inch of surface area.

In another embodiment, each stator hole defines an opening of not greater than 9 $mm^2$. Preferably, each stator hole defines an opening of not greater than 7.5 $mm^2$, more preferably not greater than 7 $mm^2$, and most preferably not greater than 6.5 $mm^2$.

The stator holes can be of any shape suitable to making the desired catalyst slurry mixture. The holes can be of the same shape or varied. Non-limiting examples of various shapes can include holes that are round, oval, rectangular, pyramidal, polygonal, or any combination thereof. Preferably, a majority of the holes are a shape other than round. Polygonal shapes are particularly preferred, with polygonal being defined as a closed plane figure bounded by straight lines. More preferably, the stator includes at least one polygonal shaped hole, the polygon having at least one angle not greater than 90 degrees. Rectangular, particularly square, shapes are most preferred.

Mixing can be carried out using batch ("in-tank" type) mixing units or continuous ("in-line" type) mixing units, and the processes can be carried out quite effectively at commercial scale. In-tank mixers having the desired characteristics can function to form a slurry in a tank of from 1 gallon to 30,000 gallons. In-line mixers are preferred in that they can be used in a continuous manufacturing process. Such mixers are particularly suited for processing flow rates of slurry components of at least 100 liters per hour. Preferred rates of processing are at least 200 liters per hour. Mixers that can process slurry at rates of at least 400 liters per hour or at least 800 liters per hour can also be used.

The slurry is mixed at a relatively high viscosity and as the mixing is progressed, the viscosity preferably decreases. In one embodiment, the slurry is mixed until the viscosity is decreased by at least about 10%, preferably by at least 15%, and more preferably by at least 20%.

The slurry product should not be too viscous as formation of highly attrition resistant catalyst particles can be adversely affected. In one embodiment, the slurry is mixed to form a slurry product having a viscosity of not greater than 10,000 cP. Preferably, the slurry product has a viscosity of not greater than 9000 cP, more preferably not greater than 8000 cP.

The slurry product should also be sufficiently viscous as formation of catalyst particles during spray drying can be difficult. In one embodiment, the slurry product has a viscosity of at least 500 cP. Preferably, the slurry product has a viscosity of at least 600 cP, more preferably at least 700 cP.

The slurry can be mixed using a batch type mixing process or using an in-line mixing process. In-line mixing can be accomplished using no recyle or using recyle. In a preferred embodiment, recycling is used. Preferably, the molecular sieve crystals, clay, binder and liquid are mixed with an in-line rotor-stator mixer applying recycle at a number of passes of at least 1, more preferably at least 2, and most preferably at least 3.

The rotor should be rotated at a tip speed sufficient to thoroughly mix the slurry of high solids content and to ultimately provide a slurry having the desired low viscosity. Tip speed (v, in m/sec) is defined as $v = \omega * \phi * \pi * 2.54/100/60$, where $\omega$ is rotation speed in rpm and $\phi$ is rotor diameter in inches. In one embodiment, the rotor is rotated at a tip speed of at least 5 m/sec. Preferably, the rotor is rotated at a speed of at least 6 m/sec, more preferably at least 6.5 m/sec, and most preferably at least 7 m/sec.

III. Slurry Components

A. Overall Composition

The catalyst of this invention is a molecular sieve catalyst composition, which comprises molecular sieve crystals, clay, and binder. Such a combination is generally referred to as a formulated catalyst. In one aspect, the formulated catalyst composition is characterized by being highly resistant to attrition.

B. Molecular Sieve Crystal Component

The molecular sieve particles used to make the formulated catalyst include any of a variety of molecular sieve components. The components include zeolites or non-zeolites, preferably non-zeolites. In one embodiment, the molecular sieves are small pore non-zeolite molecular sieves having an average pore size of less than about 5 angstroms, preferably an average pore size ranging from about 3 to 5 angstroms, more preferably from 3.5 to 4.2 angstroms. These pore sizes are typical of molecular sieves having 8 membered rings.

Conventional crystalline aluminosilicate zeolites having catalytic activity are desirable molecular sieves that can be used in making the catalyst of this invention. Non-limiting examples of zeolites which can be employed in the practice of this invention, include both natural and synthetic zeolites. These zeolites include zeolites of the structural types included in the *Atlas of Zeolite Framework Types*, edited by Ch. Baerlocher, W. M. Meier, D. H. Olson, Fifth Revised edition, Elsevier, Amsterdam, 2001.

Additional examples of molecular sieve particles used to make formulated molecular sieve catalyst according to this invention include zeolite as well as non-zeolite molecular sieves, and are of the large, medium, or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG; THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW, and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM, and TON. In one preferred embodiment, the molecular sieve of the invention has an AEI topology or a CHA topology, or a combination thereof, most preferably a CHA topology.

Metalloaluminophosphate molecular sieves are particularly preferred molecular sieves used in the manufacturing process of this invention. In one embodiment, these particles are represented by the empirical formula, on an anhydrous basis:

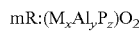

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB, and Lanthanide's of the Periodic Table of Elements, preferably M is selected from one of the group consisting of Si, Ge, Co, Cr, Cu, Fe, Ga, Ge, Mg, Mn, Ni, Sn, Ti, Zn, Zr, and mixtures thereof. In a particular embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Other examples of metalloaluminophosphate molecular sieves useful in the process of this invention include those described in EP-0 888 187 B1 (microporous crystalline metallophosphates, $SAPO_4$ (UIO-6)), U.S. Pat. No. 6,004,898 (molecular sieve and an alkaline earth metal), PCT WO 01/62382 published Aug. 30, 2001 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

Most preferably, the metalloaluminophosphate molecular sieve crystals present in the molecular sieve catalyst composition are selected from the group consisting of silicoaluminophosphate (SAPO) molecular sieves, aluminophosphate molecular sieves, and metal substituted forms thereof. Non-limiting examples of SAPO and AlPO molecular sieves that may be present in the molecular sieve catalyst of the invention include molecular sieves selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal containing molecular sieves thereof, and mixtures thereof. The more preferred molecular sieves include molecular sieves selected from the group consisting of SAPO-18, SAPO-34, SAPO-35, SAPO-44, SAPO-56, AlPO-18 AlPO-34, metal containing molecular sieves thereof, and mixtures thereof; even more preferably molecular sieves selected from the group consisting of SAPO-18, SAPO-34, AlPO-34, AlPO-18, metal containing molecular sieves thereof, and mixtures thereof; and most preferably molecular sieves selected from the group consisting of SAPO-34, AlPO-18, metal containing molecular sieves thereof, and mixtures thereof.

As used herein, the term mixture is synonymous with combination and is considered a composition of matter having two or more components in varying proportions, regardless of their physical state. With regard to the molecular sieve crystal components of the catalyst, the term further encompasses physical mixtures of crystalline and amorphous components, as well as intergrowths of at least two different molecular sieve structures, such as, for example those described in PCT Publication No. WO 98/15496.

In one embodiment, the molecular sieve crystal is an intergrowth material having two or more distinct phases of crystalline structures within one molecular sieve composition. In another embodiment, the molecular sieve crystal comprises at least one intergrown phase of AEI and CHA framework-types. For example, SAPO-18, AlPO-18 and RUW-18 have an AEI framework-type, and SAPO-34 has a CHA framework-type. In a further embodiment, the molecular sieve crystal comprises a mixture of intergrown material and non-intergrown material.

C. Clay Component

The clay component of the catalyst of this invention can be a natural or synthetic clay. Naturally occurring clays or modified natural occurring clays, e.g., partially dried or dehydrated, milled or micronized, or chemically treated are preferred. Such naturally occurring clays include clays from the kaolinite group, the mica group, the smectite group, and the chlorite group. Examples of kaolinite group clays include kaolinite, dickite and halloysite. Examples of the mica group clays include muscovite, illite, glauconite and biotite. Examples of the smectite group include montmorillonite and vermiculite. Examples of the chlorite group include penninite, clinochlore, ripidolite and chamosite.

Mixed layer clays can also be used. These clays are made of a regular or random stacking of layers composed of members of one or more groups of clay minerals. Chlorite may be seen as a regular alternation of mica and brucite layers. Random mixed layering of three layer clays is common, with examples being mixed layer mica/smectite and chlorite/vermiculite. In regular mixed layer structures such as chlorite, the basal spacing is a combination of that of the individual layers. In random mixed layering there is a non-integral series of reflections from the basal planes. This is shown as a composite reflection intermediate in position between those of the individual layers, or as a spreading of the reflection. Thus, when a significant amount of smectite is interlayered with mica in a random manner, the mica peak will not be sharp, but will be spread toward the lower angle smectite reflection. The amount of spreading depends on the amount of mixed layering that exists.

D. Binder Component

Binders that are used in this invention are materials that act like glue, binding together the molecular sieve crystals and other materials, to form a formulated molecular sieve catalyst composition. Non-limiting examples of binders that can be used in this invention include various types of inorganic oxide sols such as an inorganic oxide sol of alumina or silica, and, in particular, aluminum chlorohydrate, hydrated aluminas, silicas, and/or other inorganic oxide sols.

E. Catalyst Composition Characteristics

One characteristic of the formulated catalyst composition of this invention is that it is highly attrition resistant, as measured by the Attrition Rate Index (ARI) method. The ARI is used over other measurement methods, since many other methods are not sufficient to measure very highly attrition resistant molecular sieve catalysts such as those made according to this invention.

The ARI methodology is similar to the conventional Davison Index method. The smaller the ARI is, the more resistant to attrition the catalyst is. The ARI is measured by adding 6.0±0.1 g of catalyst having a particles size ranging from 53 to 125 microns to a hardened steel attrition cup. Approximately 24,000 scc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent catalyst that has broken apart through attrition.

The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in wt %/hr.

$$ARI = C/(B+C)/D \times 100\%$$

wherein
B=weight of catalyst left in the cup after the attrition test,
C=weight of collected fine catalyst particles after the first hour of attrition treatment, and
D=duration of treatment in hours after the first hour attrition treatment.

In one embodiment, the formulated catalyst composition has an attrition resistance index of not greater than 2 wt %/hr. Preferably, wherein the catalyst composition has an attrition resistance index (ARI) of not greater than 1.5 wt %/hr, and more preferably not greater than 1 wt %/hr.

The catalyst composition of the invention also has a relatively high density relative to conventional catalysts. In particular, the catalyst composition of the invention has a relatively high apparent bulk density (ABD) relative to conventional catalysts.

According to the invention, one way of measuring ABD was using the following procedure. A KIMAX graduated cylinder from KAMLE USA, accurate to 0.05 cc and having a 25 cc capacity, was used to weigh catalyst. The empty cylinder was weighed and the weight recorded as $W_a$. Approximately 25 cc of spray dried and calcined catalyst was poured into the cylinder, and the cylinder was tapped against a lab bench surface at a frequency of 160-170 times per minute for 30 seconds to pack the cylinder into the cylinder. The weight of the packed cylinder was weighed and recorded as $W_b$. The volume of the catalyst in the cylinder was determined by reading the level of the packed catalyst in the cylinder and recorded as $V_c$. ABD was then calculated as $ABD=(W_b-W_a)/V_c$.

In one embodiment, the catalyst composition has an apparent bulk density (ABD) of at least 0.78 g/cc. Preferably, the catalyst composition has an ABD of at least 0.79 g/cc, more preferably at least 0.8 g/cc, and most preferably at least 0.81 g/cc. Generally, the catalyst density is not significantly greater than water. In one embodiment, the catalyst composition has an ABD not greater than 1 g/cc. Preferably, the catalyst composition has an ABD not greater than 0.99 g/cc, and more preferably not greater than 0.98 g/cc.

The catalyst composition of this invention is a dried catalyst composition. It can be dried so that it retains a template within the pore structure of the molecular sieve component, such as by spray drying, or it can be further dried, such as by calcining, which removes the template from the pore structure. Because the dried catalyst is attrition resistant, it is not necessary to calcine the formulated composition prior to use. For example, the dried composition can be loaded into a reaction system so that conditions within the system remove the template to activate the catalyst for use during operation of the reaction process.

IV. Making Formulated Molecular Sieve Catalyst

A. Components of Formulated Molecular Sieve Catalyst

Molecular sieve catalyst, which contains molecular sieve crystal product, binder and matrix materials, is also referred to as a formulated catalyst. It is made by mixing together molecular sieve crystals (which preferably includes template) and a liquid (preferably water), with matrix material and binder, to form a slurry. The slurry is then dried (i.e., liquid is removed). Preferably, the slurry is dried without completely removing the template from the molecular sieve, such as by spray drying. Then, the spray dried catalyst is calcined to remove additional water and the template material. Once template material is removed, the catalyst is considered activated.

The liquid used to form the slurry can be any liquid conventionally used in formulating molecular sieve catalysts. Non-limiting examples of suitable liquids include water, alcohol, ketones, aldehydes, esters, or a combination thereof. Water is a preferred liquid. The water can come from a variety of sources, including from process water of an oxygenate to olefins reaction process. In the oxygenate to olefins process, a substantial amount of water is produced. With some clean-up, e.g., removal of solids and hydrocarbon contaminants, the water can be re-used in a variety of ways, including making the slurry solution. The water can also be used in the direct manufacture of the molecular sieve itself.

Matrix materials are preferably included in the slurry. Such materials are typically effective in the formulated molecular sieve catalyst product as thermal sinks assisting in shielding heat from the catalyst composition, for example, during regeneration. They can further act to densify the catalyst composition, increase catalyst strength such as crush strength and attrition resistance, and to control the rate of conversion in a particular process. Non-limiting examples of matrix materials include one or more of: rare earth metals, metal oxides including titania, zirconia, magnesia, thoria, beryllia, quartz, silica or sols, and mixtures thereof; for example, silica-magnesia, silica-zirconia, silica-titania, silica-alumina, and silica-alumina-thoria.

One preferred type of matrix material used to make the catalyst of this invention is clay. Particularly preferred clays include kaolins such as, for example, Dixie, McNamee, Georgia, and Florida clays. Optionally, the matrix material, preferably any of the clays, are calcined, acid treated, and/or chemical treated before being used as a slurry component.

In a particular embodiment, the clay has a low iron or titania content, and is most preferably kaolin clay. Kaolin has been found to form a pumpable, high solid content slurry; it has a low fresh surface area, and it packs together easily due to its platelet structure.

Preferably, the clay has an average particle size of from about 0.05 µm to about 0.75 µm; more preferably from about 0.1 µm to about 0.6 µm. It is also desirable that the clay material have a $d_{90}$ particle size distribution of less than about 1.5 µm, preferably less than about 1 µm.

Binders are also included in the slurry used to make the formulated molecular sieve catalyst of this invention. In one embodiment of the invention, the binder is an alumina-containing sol, preferably aluminium chlorohydrate. Upon calcining, the inorganic oxide sol, is converted into an inorganic oxide matrix component, which is particularly effective in forming an attrition resistant molecular sieve catalyst composition. For example, an alumina sol will convert to an aluminium oxide matrix following heat treatment.

Aluminium chlorohydrate, a hydroxylated aluminium based sol containing a chloride counter ion, also known as aluminium chlorohydrol, has the general formula

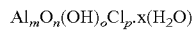
$Al_mO_n(OH)_oCl_p\cdot x(H_2O)$ wherein m is 1 to 20, n is 1 to 8, o is 5 to 40, p is 2 to 15, and x is 0 to 30. In one embodiment, the binder is $Al_{13}O_4$ $(OH)_{24}Cl_7 \cdot 12(H_2O)$ as is described in G. M. Wolterman, et al., *Stud. Surf. Sci. and Catal.*, Vol. 76, pp. 105-144, Elsevier, Amsterdam, 1993, which is herein incorporated by reference. In another embodiment, one or more binders are present in combination with one or more other non-limiting examples of alumina materials such as aluminium oxyhydroxide, γ-alumina, boehmite and transitional aluminas such as β-alumina, γ-alumina, δ-alumina, ε-alumina, κ-alumina, and ρ-alumina, aluminium trihydroxide, such as gibbsite, bayerite, nordstrandite, doyelite, and mixtures thereof.

Aluminum chlorohydrate can be prepared by dissolving either metallic aluminum or hydrated alumina in hydrochloric acid under controlled conditions, and is available commercially in different forms, such as solid products; for example, the solid of chemical formula $Al_2(OH)_5Cl\cdot n(H_2O)$ or as pre-prepared, commercially available, aqueous solutions. Other non-limiting examples of useful aluminum oxide precursors that may be used according to this invention include aluminum hexahydrate, aluminum pentachlorohydrate ($Al_2(OH)Cl_5$), aluminum tetrachlorohydrate ($Al_2(OH)_2Cl_4$), aluminum trichlorohydrate ($Al_2(OH)_3Cl_3$), aluminum dichlorohydrate ($Al_2(OH)_4Cl_2$), aluminum sesquichlorohydrate ($Al_2(OH)_{4.5}Cl_{1.5}$).

Other non-limiting examples of binders useful according to this invention include precursors of aluminum-zirconium oxides. Such precursors include, but are not limited to, aluminum zirconium chlorohydrates; for example, aluminum zirconium trichlorohydrate, aluminum zirconium tetrachlorohydrate, aluminum zirconium pentachlorohydrate, aluminum zirconium octachlorohydrate, aluminum zirconium chlorhydrex, aluminum zirconium chlorhydrex glycine complexes (e.g., aluminum zirconium trichlorohydrex glycine complex, aluminum zirconium tetrachlorohydrex glycine complex, aluminum zirconium pentachlorohydrex glycine complex, and aluminum zirconium octachlorohydrex glycine complex). In the absence of glycine, these materials form gels in aqueous solutions. Reheis Chemicals Inc., Berkeley Heights, N.J. produces a variety of aluminum zirconium chlorohydrates. These materials can be prepared from a variety of zirconium starting materials such as zirconyl chloride ($ZrOCl_2$), zirconyl hydroxychloride (ZrO(OH)Cl), zirconium hydroxy carbonate paste (ZrO(OH)$(CO_3)_{0.5}$), and combinations of these zirconium starting materials, with a hydrated aluminum solution, such as a solution of aluminum chlorohydrate, aluminum hexahydrate, aluminum sesquichlorohydrate or aluminum dichlorohydrate solution, or a solution obtained by combining one or several of these aluminum species solutions.

In another embodiment, the binders are alumina sols, predominantly comprising aluminium oxide, optionally, including silicon. In yet another embodiment, the binders are peptised alumina made by treating alumina hydrates such as pseudobohemite, with an acid, preferably a non-halogen acid, to prepare sols or aluminium ion solutions. Non-limiting examples of commercially available colloidal alumina sols include Nalco 8676 available from Nalco Chemical Co., Naperville, Ill., and Nyacol available from the Nyacol Nano Technology Inc., Boston, Mass.

In a preferred embodiment, the amount of binder used to prepare the molecular sieve catalyst composition is at least 5 wt %, based on total weight of the material used to make the composition, excluding liquid (i.e., after drying), particularly excluding water. Preferably the amount of binder used to prepare the molecular sieve catalyst is at least 8 wt %, and more preferably at least 10 wt %, based on total weight of the material used in making the catalyst, excluding liquid (i.e., after drying). It is also preferred that the amount of binder used to prepare the molecular sieve catalyst is not greater than about 50 wt %, preferably not greater than 40 wt %, and more preferably not greater than 30 wt %, based on total weight of the material used in making the catalyst, excluding liquid (i.e., after drying).

B. Making a Slurry with Molecular Sieve Crystals

The molecular sieve crystals are mixed with clay and binder, as well as liquid solvent component, to form a slurry. The components can be mixed in any order. In a particular embodiment, binder is added to a liquid, molecular sieve then added, followed by clay addition. The mixture is thoroughly stirred, preferably using a rotor-stator mixing unit having appropriate characteristics to form the slurry. Examples of desired characteristics are detailed above.

The molecular sieve crystals, clay, and binder are mixed together to form a slurry having a desired solids content. The solids content should be sufficiently high, otherwise a less attrition resistant catalyst will be formed.

In one embodiment, molecular sieve crystals, clay, and binder are mixed together to form a slurry having a solids content of at least 40 wt %, based on total weight of the slurry mixture. Preferably, molecular sieve crystals, clay, binder and water are mixed to form a slurry having a solids content of at least 41 wt %, more preferably at least 43 wt %, and most preferably at least 44 wt %, based on the total weight of the slurry.

The solids content can be measured using any conventional means. However, a CEM MAS 700 microwave muffle furnace (CEM Corp., Matthews, N.C.) is particularly preferred to give results consistent with the values recited herein. It is also preferred that the slurry have a solids content of not greater than 60 wt %, based on total weight of the slurry. Preferably, the slurry has a solids content of not greater than 58 wt %, more preferably not greater than 56 wt %, and most preferably not greater than 54 wt % based on total weight of the slurry.

In another embodiment of the invention, the molecular sieve crystals, clay, and binder are mixed together to form a slurry mixture at a binder to molecular sieve weight ratio of at least 0.20:1. Preferably, the molecular sieve crystals, clay, and binder are mixed together at a binder to molecular sieve weight ratio of at least 0.22:1, more preferably at least 0.24:1, and most preferably at least 0.25:1. It is also preferred that the crystals, clay, and binder be mixed together at a binder to molecular sieve weight ratio of not greater than 0.8:1, preferably not greater than 0.6:1.

In another embodiment, the molecular sieve crystals, clay, and binder are mixed together to form a slurry mixture at a binder content of at least 5 wt %, preferably at least 8 wt %, and more preferably at least 10 wt %, based on total weight of the mixture, excluding liquid (e.g., water). It is also preferred in an embodiment that the molecular sieve crystals, clay, and binder are mixed together to form a slurry mixture at a binder content of not greater than 30 wt %, preferably not greater than 25 wt %, based on total weight of the mixture, excluding liquid (e.g., water).

The temperature at which the slurry is made can range. Examples of such conditions include temperatures ranging from 0° C. to 100° C., preferably of from 10° C. to 90° C., more preferably of from 15° C. to 80° C., most preferably of from 20° C. to 70° C.

In-tank or batch operation can be operated for some duration to ensure proper mixing and viscosity. In one embodiment, the rotor-stator mixer is in-tank operated for a period of at least 2 hours, preferably at least 4 hours, more preferably at least 5 hours, and most preferably at least 6 hours. In a preferred embodiment, mixing of slurry components is performed for not more than 150 hours, preferably not more than 120 hours, most preferably not more than 100 hours. Other preferred batch mixing conditions include mixing at a temperature of from 30° C. to 50° C. for a period of from 4 hours to 80 hours, preferably from 5 hours to 75 hours, more preferably of from 5.5 hours to 50 hours, most preferably of from 6 hours to 36 hours.

C. Drying the Slurry

In one embodiment, the slurry of the molecular sieve, binder, and matrix materials is fed to a forming unit that produces a dried molecular sieve catalyst composition. Non-limiting examples of forming units include spray dryers, pelletizers, extruders, etc. In a preferred embodiment, the forming unit is spray dryer. Typically, the forming unit is maintained at a temperature sufficient to remove most of the liquid (e.g., water) from the slurry.

When a spray dryer is used as the forming (or drying) unit, typically, the slurry of the molecular sieve, matrix material and binder, is co-fed to the drying unit with a drying gas. In one embodiment the drying unit has an average inlet temperature ranging from 150° C. to 550° C., and an average outlet temperature ranging from 100° C. to about 250° C.

In one embodiment, the slurry is passed through a nozzle distributing the slurry into small droplets, resembling an aerosol spray, into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a partially, substantially or totally dried molecular sieve catalyst composition.

In another embodiment of the invention, the slurry is dried in a drying unit and then calcined. In one embodiment, the slurry is dried to form a dried molecular sieve catalyst composition, and the dried catalyst composition is calcined. In general, calcination further hardens and/or activates the dried molecular sieve catalyst composition. An acceptable calcination environment is air that typically includes a small amount of water vapour. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), steam, or any combination thereof.

The dried or formulated molecular sieve catalyst composition can be calcined in many types of devices, including but not limited to, rotary calciners, fluid bed calciners, batch ovens, and the like. Calcination time is typically dependent on the degree of hardening of the molecular sieve catalyst composition and the temperature.

In a preferred embodiment, the molecular sieve catalyst composition is heated in nitrogen at a temperature of from about 600° C. to about 700° C. Heating is carried out for a period of time typically from 1 minute to 15 hours, preferably from 2 minutes to about 10 hours, more preferably from about 3 minutes to about 5 hours, and most preferably from about 5 minutes to about 4 hours.

V. Methods of using Catalyst

The molecular sieve catalyst product made according to this invention is useful in a variety of processes including cracking of, for example, a naphtha feed to light olefin(s) (U.S. Pat. No. 6,300,537) or higher molecular weight (MW) hydrocarbons to lower MW hydrocarbons; hydrocracking of, for example, heavy petroleum and/or cyclic feedstock; isomerization of, for example, aromatics such as xylene; polymerization of, for example, one or more olefin(s) to produce a polymer product; reforming; hydrogenation; dehydrogenation; dewaxing of, for example, hydrocarbons to remove straight chain paraffins; absorption of, for example, alkyl aromatic compounds for separating out isomers thereof; alkylation of, for example, aromatic hydrocarbons such as benzene and alkyl benzene, optionally with propylene to produce cumene or with long chain olefins; transalkylation of, for example, a combination of aromatic and polyalkylaromatic hydrocarbons; dealkylation; hydrodecyclization; disproportionation of, for example, toluene to make benzene and paraxylene; oligomerization of, for example, straight and branched chain olefin(s); and dehydrocyclization.

Preferred processes include processes for converting naphtha to highly aromatic mixtures; converting light olefin(s) to gasoline, distillates and lubricants; converting oxygenates to olefin(s); converting light paraffins to olefins and/or aromatics; and converting unsaturated hydrocarbons (ethylene and/or acetylene) to aldehydes for conversion into alcohols, acids, and esters.

The most preferred process of the invention is a process directed to the conversion of a feedstock to one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms. Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

The catalyst made according to the process of this invention has an attrition resistance that is suitable for use in a wide variety of reaction processes. Examples of such processes include a fixed-bed process, or more typically as a fluidized-bed process (including a turbulent-bed process), such as a continuous fluidized-bed process, and particularly a continuous high-velocity, fluidized-bed process.

VI. Examples of Methods of Making Slurry and Catalyst

EXAMPLES 1-6

Examples 1-6 show the rheological behavior of a catalyst formulation using an intergrown AEI/CHA molecular sieve, wherein slurry viscosity decreases as function of milling (number of passes). The components of the formulation are mixed using a Silverson L4RT-A in-line mixer (rotor size: 1.25", Silverson Machines, Inc., East Longmeadow, Mass.) at 6000-7500 RPM using a square hole screen (gap size: 3/1000"). The viscosity results of a 44.87-45.41% solids content slurry containing 45% molecular sieve, 13.5% aluminum chlorohydrate (ACH, Reheis, Inc., Berkeley Heights, N.J.) and 41.5% kaolin clay (ASP Ultrafine, Engelhard Corp., Rosewell, Ga.), based on total weight of the slurry excluding liquid, are given in Table 1.

TABLE 1

| | Milling and Slurry Conditions | | | Product and Slurry Properties | | |
|---|---|---|---|---|---|---|
| Ex. No. | Number of Passes | Solids Content wt % | Milling (RPM) | ABD (g/cc) | ARI (wt %/hr) | Micropore Surface Area ($m^2/g$) | Viscosity (cP; @ 10 RPM) |
| 1 | 0 | 45.04 | 6000 | 0.77 | 2.41 | 231 | 10700 |
| 2 | 3 | 44.89 | 6000 | 0.79 | 2.02 | 230.9 | 9500 |
| 3 | 15 | 45.41 | 6000 | 0.78 | 1.59 | 228.8 | 7400 |
| 4 | 30 | 45.05 | 7500 | 0.83 | 0.78 | 231.8 | 6400 |
| 5 | 60 | 44.87 | 7500 | 0.83 | 0.42 | 223.7 | 3200 |
| 6 | 100 | 45.25 | 7500 | 0.83 | 0.47 | 232 | 2900 |

EXAMPLE 7

This example shows the rheological behavior of a catalyst formulation using an intergrown AEI/CHA molecular sieve, wherein slurry viscosity increases as function of milling (number of passes). The components of the formulation are mixed using a Silverson 150L in-line mixer (rotor size: 1.5") at 5000 RPM using a round hole screen (gap size: 7/1000"). The viscosity results of a 42.3% solids content slurry containing 45% molecular sieve, 13.5% aluminum chlorohydrate (ACH) and 41.5% kaolin clay, based on total weight of the slurry excluding liquid, are given in Table 2.

TABLE 2

| Number of Passes | Viscosity (cP; @ 10 RPM) |
|---|---|
| 2.5 | 4256 |
| 10 | 4544 |
| 25 | 4487 |
| 55 | 5243 |

EXAMPLE 8

This example shows the rheological behavior of a catalyst formulation using an intergrown AEI/CHA molecular sieve, wherein slurry viscosity increases as function of milling (number of passes). The components of the formulation are mixed using a Silverson 150L in-line mixer (rotor size: 1.5") at 5000 RPM using a round hole screen (gap size: 7/1000").

The viscosity results of a 43.7% solids content slurry containing 45% molecular sieve, 13.5% aluminum chlorohydrate (ACH) and 41.5% kaolin clay, based on total weight of the slurry excluding liquid, are given in Table 3.

TABLE 3

| Number of Passes | Viscosity (cPs; @ 10 RPM) |
| --- | --- |
| 2.5 | 7019 |
| 25 | 8253 |
| 85 | 8952 |
| 105 | 9175 |

EXAMPLE 9

This example shows the rheological behavior of a catalyst formulation using an intergrown AEI/CHA molecular sieve, wherein slurry viscosity decreases as function of milling (number of passes). The components of the formulation are mixed using a Silverson 150L in-line mixer (rotor size: 1.5") at 5000 RPM using a square hole screen (gap size: 3/1000"). The viscosity results of a 41.2% solid content slurry containing 45% molecular sieve, 13.5% aluminum chlorohydrate (ACH) and 41.5% kaolin clay, based on total weight of liquid, are given in Table 4.

TABLE 4

| Number of Passes | Solids Content (wt. %) | Viscosity (cP; @ 10 RPM) |
| --- | --- | --- |
| 0 | 41.2 | 15513 |
| 1 | 41.2 | 13558 |
| 12 | 41.2 | 11803 |
| 27 | 41.2 | 9881 |
| 40 | 41.2 | 8648 |
| 65 | 41.2 | 6921 |

The data in the tables indicate that, in general, slurry viscosity increases as milling increases when only round hole stators are used. Slurries having very high viscosities are not as desirable, because slurries with relatively high viscosities are difficult to process (e.g., hard to pump). In addition, high viscosity slurries will tend to produce dried catalyst particles that are more susceptible to attrition, i.e., have higher attrition rate indices (ARIs).

The principles and modes of operation of this invention have been described above with reference to various exemplary and preferred embodiments. As understood by those of skill in the art, the overall invention, as defined by the claims, encompasses other preferred embodiments not specifically enumerated herein.

What is claimed is:

1. A method of making an attrition resistant molecular sieve catalyst composition, comprising the steps of:
    a) mixing together molecular sieve crystals, clay, binder, and liquid with a rotor-stator mixer to form a slurry having a solids content of at least 40 wt %, based on total weight of the slurry;
    b) progressing the mixing until slurry viscosity decreases; and
    c) drying the slurry to produce a dried molecular sieve catalyst composition having an attrition rate index of not greater than 2 wt %/hr.

2. The method of claim 1, wherein the slurry is mixed until the viscosity is decreased by at least about 10%.

3. The method of claim 2, wherein the slurry is mixed until the viscosity is decreased by at least 15%.

4. The method of claim 3, wherein the slurry is mixed until the viscosity is decreased by at least 20%.

5. The method of claim 1, wherein the stator has at least one polygonal shaped hole defining an opening of not greater than 9 mm$^2$.

6. The method of claim 5, wherein the at least one polygonal shaped hole has at least one angle not greater than 90 degrees.

7. The method of claim 6, wherein the at least one polygonal shaped hole is a rectangle.

8. The method of claim 7, wherein the at least one polygonal shaped hole is a square.

9. The method of claim 5, wherein the rotor and stator have a gap distance of not greater than 0.3 mm.

10. The method of claim 9, wherein the rotor and stator have a gap distance of not greater than 0.28 mm.

11. The method of claim 5, wherein each hole defines an opening of not greater than 7.5 mm$^2$.

12. The method of claim 5, wherein the stator has at least 4 holes per square inch of surface area.

13. The method of claim 1, wherein the molecular sieve crystals, clay, binder, and liquid are mixed with an in-line rotor-stator mixer applying recycle at a number of passes of at least 1.

14. The method of claim 1, wherein the rotor is rotated at a tip speed of at least 5 m/sec.

15. The method of claim 1, wherein the slurry is dried by a combination of spray drying and calcining.

16. The method of claim 1, wherein the molecular sieve crystals, clay, binder, and liquid are mixed to form a slurry having a viscosity of not greater than 10,000 cP.

17. The method of claim 1, wherein the clay is a natural or synthetic clay.

18. The method of claim 1, wherein the binder is an inorganic oxide sol of alumina or silica.

19. The method of claim 1, wherein the molecular sieve crystals, clay, binder, and liquid are mixed together to form a slurry having a viscosity of at least 500 cP.

20. The method of claim 1, wherein the molecular sieve crystals, clay, binder, and liquid are mixed together to form a slurry having a solids content of not greater than 60 wt %, based on total weight of the slurry.

21. The method of claim 1, wherein the molecular sieve particles are metalloaluminophosphate molecular sieve crystals.

22. The method of claim 21, wherein the metalloaluminophosphate molecular sieve crystals are selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal containing molecular sieves thereof, and mixtures thereof.

23. The method of claim 22, wherein the dried metalloaluminophosphate molecular sieve catalyst is contacted with oxygenate to form olefin product.

24. A process for making olefin product, comprising the steps of:
    a) mixing together metalloaluminophosphate molecular sieve crystals, clay, binder, and liquid with a rotor-stator mixer to form a slurry having a solids content of at least 40 wt %, based on total weight of the slurry, and a viscosity of not greater than 10,000 cP, wherein the rotor and stator have a gap distance of not greater than 0.3 mm and the stator has a plurality of polygonal shaped holes, each hole defining an opening of not greater than 9 mm$^2$;

b) drying the slurry to produce a dried molecular sieve catalyst composition having an attrition rate index of not greater than 2 wt %/hr;

c) contacting the dried metalloaluminophosphate molecular sieve catalyst with oxygenate to form olefin product.

25. The method of claim 24, wherein the at least one polygonal shaped hole has at least one angle not greater than 90 degrees.

26. The method of claim 25, wherein the at least one polygonal shaped hole is a rectangle.

27. The method of claim 26, wherein the at least one polygonal shaped hole is a square.

28. The method of claim 24, wherein the rotor and stator have a gap distance of not greater than 0.28 mm.

29. The method of claim 24, wherein each hole defines an opening of not greater than 7.5 mm$_2$.

30. The method of claim 24, wherein the stator has at least 4 holes per square inch of surface area.

* * * * *